(12) United States Patent
Kim (10) Patent No.: US 9,588,237 B2
(45) Date of Patent: Mar. 7, 2017

(54) DIGITAL X-RAY DETECTOR AND METHOD FOR MANUFACTURING THE X-RAY DETECTOR

(71) Applicant: Hydis Technologies Co., Ltd., Incheon-si (KR)

(72) Inventor: Seongsu Kim, Icheon-si (KR)

(73) Assignee: Hydis Technologies Co., Ltd., Icheon-Si (KR)

( * ) Notice: Subject to any disclaimer, the term of this patent is extended or adjusted under 35 U.S.C. 154(b) by 0 days.

(21) Appl. No.: 15/010,270

(22) Filed: Jan. 29, 2016

(65) Prior Publication Data
US 2016/0223692 A1 Aug. 4, 2016

(30) Foreign Application Priority Data
Jan. 30, 2015 (KR) .................. 10-2015-0014944

(51) Int. Cl.
| | |
|---|---|
| *H01L 31/036* | (2006.01) |
| *G01T 1/24* | (2006.01) |
| *H01L 27/146* | (2006.01) |
| *H01L 31/117* | (2006.01) |
| *A61B 6/00* | (2006.01) |

(52) U.S. Cl.
CPC .............. *G01T 1/244* (2013.01); *G01T 1/241* (2013.01); *H01L 27/14603* (2013.01); *H01L 27/14623* (2013.01); *H01L 27/14632* (2013.01); *H01L 27/14636* (2013.01); *H01L 27/14659* (2013.01); *H01L 27/14687* (2013.01); *H01L 31/117* (2013.01); *A61B 6/4233* (2013.01); *H01L 27/14689* (2013.01)

(58) Field of Classification Search
CPC ......... H01L 27/14636; H01L 27/14659; H01L 31/117; H01L 27/14612; H01L 27/14689; H01L 27/14623; H01L 27/14685; H01L 27/1462
See application file for complete search history.

(56) References Cited

U.S. PATENT DOCUMENTS

| | | | |
|---|---|---|---|
| 8,785,994 B2* | 7/2014 | Kim ...................... | H01L 31/118 257/292 |
| 2010/0163882 A1* | 7/2010 | Jung .................. | H01L 27/14632 257/59 |
| 2014/0145252 A1* | 5/2014 | Kim ...................... | H01L 27/308 257/292 |

* cited by examiner

*Primary Examiner* — Thanh Y Tran
(74) *Attorney, Agent, or Firm* — The Webb Law Firm (57) ABSTRACT

Provided herein is a digital x-ray detector wherein a plurality of sensing pixels are formed in a matrix structure, and wherein a pin structure positioned in an odd number line and a pin structure positioned in an even number line are not formed in the same process, thereby preventing a line detect by a particle.

18 Claims, 7 Drawing Sheets

FIG. 1A
100

PRIOR ART

FIG. 1B

PRIOR ART

FIG. 3 ns.com. DIGITAL X-RAY DETECTOR AND METHOD
FOR MANUFACTURING THE X-RAY
DETECTOR

CROSS-REFERENCE TO RELATED APPLICATION

This application claims priority to Korean Patent Application No. 10-2015-0014944 filed Jan. 30, 2015, the disclosure of which is hereby incorporated in its entirety by reference.

BACKGROUND

1. Field

The following description relates to a digital x-ray detector, and more particularly, to a digital x-ray detector capable of preventing line defects in the digital x-ray detector, and a method for manufacturing the same.

2. Description of Related Art

A digital x-ray detector is a device configured to convert x-ray that penetrated a human body into electrical signals, digitalize those electrical signals and then detect those digitalized signals. Digital x-ray detectors are used in medical inspection apparatuses, and nondestructive inspection apparatuses and the like. Digital x-ray detectors are largely classified into direct method detectors and indirect method detectors depending on the method of converting incident x-ray into electrical signals.

The direct method is a method of using external power supply to collect electrons and pairs of positive holes being generated in an x-ray receptor layer constituting a digital x-ray detector as the x-ray that penetrated a human body enters the x-ray receptor layer.

The indirect method is a method of using the radiance phenomenon that occurs as the x-ray that penetrated a human body enters an x-ray receptor layer made of a fluorescent material.

A conventional digital x-ray detector includes a plurality of lines. Each of these lines includes a plurality of sensing pixels. In a conventional digital x-ray detector, when a certain line of the plurality of lines is short-circuited with an adjacent line, all the pixels inside the short-circuited lines will be disabled, causing line defects.

Figure 1A:
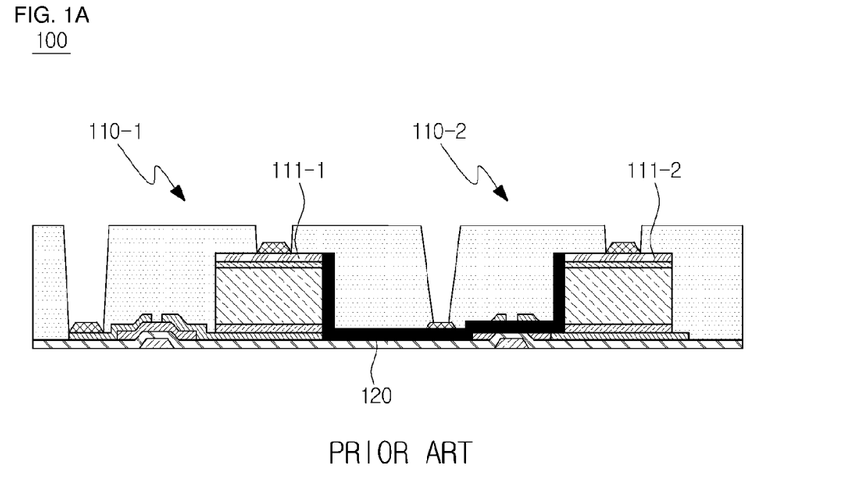
FIGS. 1A and 1B are an exemplary views of a conventional digital x-ray detector.
Figure 1B:
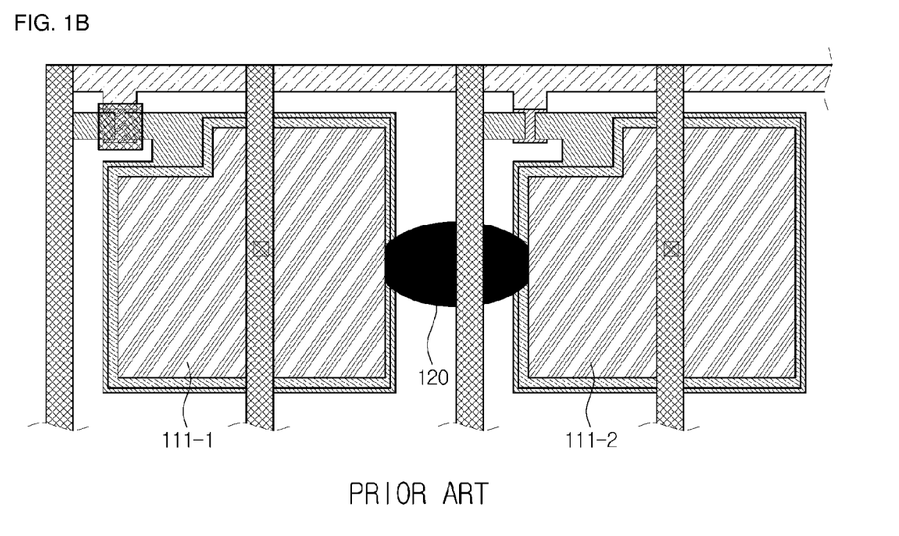

More specifically, explanation will be made on short circuits between lines in a conventional digital x-ray detector with reference to FIG. 1. FIG. 1 is an exemplary view of a conventional digital x-ray detector. Referring to FIG. 1A and FIG. 1B, after a process of manufacturing a conventional digital x-ray detector 100 is completed with a particle 120 positioned between the lines, and power is applied to test the product, a short circuit may occur due to the particle 120 between the lines, causing a line defect. In a process of manufacturing a conventional digital x-ray detector 100 with a particle positioned between the lines, a conduction may occur between an upper electrode 111-1 of a sensing pixel of an odd number line 110-1 and an upper electrode 111-2 of a sensing pixel formed on an even number line 110-2 adjacent to the odd number line 110-1 through a particle 120, thereby causing a short circuit. In this case, line defects may occur in the same odd and even number lines 110-1, 110-2 that include the short-circuited upper electrode. These odd and even number lines 110-1, 110-2 where line defects occurred are not capable of performing functions of converting x-ray into electrical signals.

Thus, there has been a need to develop a digital x-ray detector capable of preventing line defects and a manufacturing method thereof.

SUMMARY

A purpose of the present disclosure is to resolve the aforementioned problems of prior art, that is, to provide a digital x-ray detector capable of preventing lines defects, and a manufacturing method thereof.

According to an embodiment of the present disclosure, there is provided a method for manufacturing a digital x-ray detector wherein a plurality of units of sensing pixels are formed in a matrix structure, the method including forming a thin film transistor on every unit of sensing pixel area on an upper portion of a substrate; forming a first pin structure on each source electrode of a thin film transistor positioned in an odd number line; forming a first protective layer that covers an upper portion of the substrate where the first pin structures are formed; forming, on the first protective layer, a first data hole line that exposes a drain electrode of a thin film transistor positioned in the same odd number line in a row, a first bias hole line that exposes an upper electrode of the first pin structure positioned in the same odd number line in a row, a second data hole line that exposes a drain electrode of a thin film transistor positioned in the same even number line in a row, and a second pin structure hole that exposes a source electrode of a thin film transistor positioned in an even number line; forming a first data wire inside the first data hole line, and forming a first bias wire inside the first bias hole line; forming a second pin structure to be electrically connected to a source electrode of each thin film transistor exposed inside the second pint structure hole; forming a second protective layer that covers an upper portion of a substrate where the first data wire, first bias wire and second pin structure are formed; forming, on the second protective layer, a second data hole line that exposes a drain electrode of a thin film transistor positioned in the same even number line in a row and a second bias hole line that exposes an upper electrode of the second pin structure positioned in the same line in a row; and forming a second data wire inside the second data hole line and forming a second bias wire inside the second bias hole line.

The method may further include forming a light shield film that shields an upper portion of an active layer of the thin film transistor on an upper portion of the second protective layer, after the forming of a second protective layer.

The light shield film may be formed in the shape of a plurality of lines that shield the upper portion of the active layer of each thin film transistor positioned in the same odd number line and same even number line in a row.

The light shield film may be formed at the same step with the second data wire and second bias wire.

The method may further include forming a third protective layer that covers an upper portion of a substrate where the second data wire and first bias wire are formed.

According to another embodiment of the present disclosure, there is provided a digital x-ray detector where a plurality of units of sensing pixels are formed in a matrix structure, the detector including a thin film transistor formed on every unit of sensing pixel area on an upper portion of a substrate; a first pin structure formed on each source electrode of a thin film transistor positioned in an odd number line; a second pin structure formed on each source electrode of a thin film transistor positioned in an even number line; a first data wire that connects a drain electrode of a thin film transistor positioned in the same odd number line in a row; a second data wire that connects a drain electrode of a thin film transistor positioned in the same even number line in a row; a first bias wire that connects an upper electrode of the first pin structure positioned in the same odd number line in a row; a second bias wire that connects an upper electrode of the second pin structure positioned in the same even number line in a row; and a first protective layer that covers an upper portion of the substrate where the thin film transistor and first pin structure are formed, wherein the second pin structure is formed inside a hole formed in the first protective layer.

The first data wire and first bias wire may be formed inside a hole line formed in the first protective layer.

The digital x-ray detector may further include a second protective layer formed on an upper portion of the first protective layer, wherein the second data wire is formed inside a hole line formed to penetrate the first protective layer and second protective layer, and the second bias wire is formed inside a hole line formed in the second protective layer.

The digital x-ray detector may further include, on an upper portion of the second protective layer, a light shield film that shields an upper portion of the active layer of the thin film transistor.

The light shield film may be formed in the shape of a plurality of lines that shield the upper portion of the active layer of the thin film transistor positioned in the same odd number line and the same even number line in a row.

The digital x-ray detector may further include a third protective layer formed on an upper portion of the second protective layer.

According to the aforementioned various embodiments of the present disclosure, it is possible to prevent line defects between a certain line and its adjacent line of a digital x-ray detector.

DETAILED DESCRIPTION

Hereinafter, exemplary embodiments of the present disclosure will be explained in detail with reference to the illustrations in the drawings attached hereto. However, the present disclosure is not limited by the exemplary embodiments. The like reference numerals indicate the like components throughout the drawings attached.

Terms including ordinal numbers such as "first", "second" and the like may be used to explain various components, but the components are not limited by those terms. These terms are only intended to differentiate one component from other components. For example, a first component may be referred to as a second component without departing from the scope of right of the present disclosure. Likewise, a second component may be referred to as a first component. The terms used in the present application are only intended to explain a certain embodiment, and not to limit the present disclosure. Furthermore, the terms used in a singular form may include a plural form unless clearly meaning otherwise in the context.

Furthermore, throughout the present specification, "include/comprise" or "including/comprising" means that components may be further added without excluding the possibility of existence of other components.

A digital x-ray detector according to embodiments of the present disclosure includes a plurality of sensing pixels formed in a matrix structure. Each sensing pixel includes each one of a thin film transistor, lower electrode, pin structure, and upper electrode. The plurality of sensing pixels may be divided into odd number lines and even number lines.

Hereinafter, a digital x-ray detector and a manufacturing method thereof according to an embodiment of the present disclosure will be explained with reference to FIGS. 2A-2J and 3.

Figure 2A:
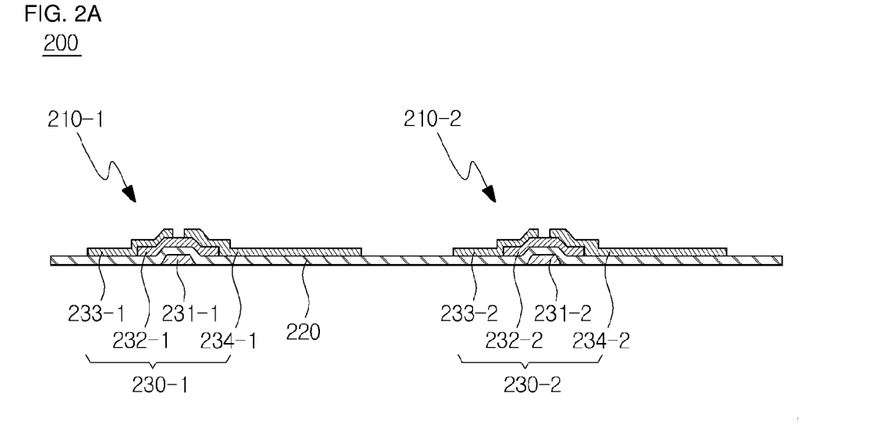
FIGS. 2A-2J are cross-section views illustrating a method for manufacturing a digital x-ray detector according to an embodiment of the present disclosure.

FIGS. 2A-2J are cross-section views illustrating a method for manufacturing a digital x-ray detector according to an embodiment of the present disclosure. Referring to FIG. 2A, first of all, there may be performed a step of forming a thin film transistor 230-1, 230-2 on every unit sensing pixel area on an upper portion of a substrate 220 of an odd number line 210-1 and even number line 210-2 of the digital x-ray detector 200 according to the embodiment of the present disclosure.

More specifically, on an upper portion of the substrate 220, on every unit sensing pixel area that is where a unit sensing pixel will be formed, a first and second thin film transistor 230-1, 230-2 that include a first and second gate electrode 231-1, 231-2, a first and second drain electrode 233-1, 233-2, a first and second source electrode 234-1, 234-2, and a first and second active layer 232-1, 232-2. Herein, a portion of the first and second source electrode 234-1, 234-2 may each be used as a lower electrode of a first pin structure 240-1 and a lower electrode of a second pin structure 240-2, respectively, that will be explained hereinafter.

Figure 2B:
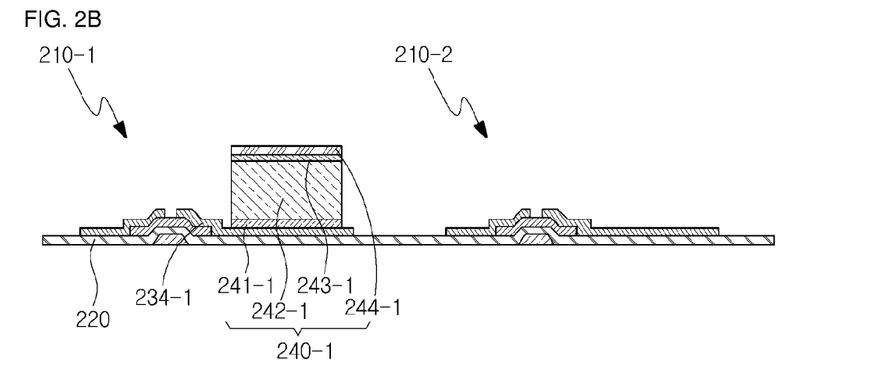

Thereafter, referring to FIG. 2B, there may be performed a step of forming the first pin structure 240-1 on each source electrode 234-1 of the thin film transistor 230-1 positioned in the odd number line 210-1.

More specifically, the first pin structure 240-1 includes a first N type semiconductor pattern 241-1 formed on a portion of the first source electrode 234-1 being used as a lower electrode (not illustrated), a first intrinsic semiconductor pattern 242-1 formed on the first N type semiconductor pattern 241-1, a first P type semiconductor pattern 243-1 formed on the first intrinsic semiconductor pattern 242-1, and a first upper electrode 244-1 formed on the first P type semiconductor pattern 243-1. Herein, the first N type semiconductor pattern 241-1 may be made of N+ a-Si, the first intrinsic semiconductor pattern 242-1 may be made of a-Si, and the first P type semiconductor pattern 243-1 may be made of P+ a-Si. Furthermore, the first upper electrode 244-1 may be made of a transparent electrode material.

Figure 2C:
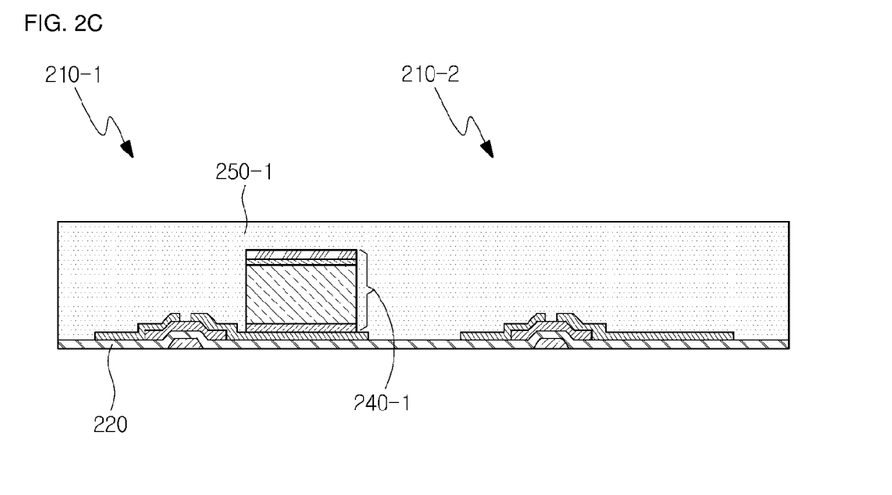

Thereafter, referring to FIG. 2C, there may be performed a step of forming a first protective layer 250-1 that covers an upper portion of the substrate 220 where the first pin structures 240-1 are formed.

More specifically, it is possible to form the first protective layer 250-1 (ILD: Inter-layer Dielectric) that covers the upper portion of the substrate 220 of the odd number line 210-1 and even number line 210-2 of the digital x-ray detector 200 where the first pin structures 240-1 are formed. Herein, the first protective layer 250-1, and a second protective layer 250-2 and third protective layer 250-3 that will be explained hereinafter may be made of any one of SiO$_2$, SiNs and SiOn.

Figure 2D:
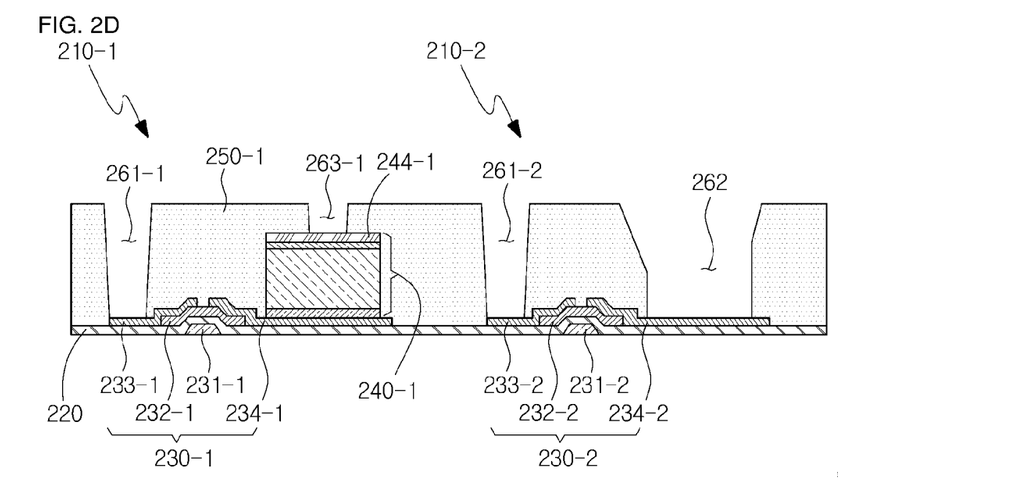

Thereafter, referring to FIG. 2D, there may be performed a step of forming, on the first protective layer 250-1, a first data hole line 261-1 for exposing the drain electrode 233-1 of the thin film transistor 230-1 positioned in the same odd number line 210-1 in a row, a first bias hole line 263-1 for exposing the upper electrode 244-1 of the first pin structure 240-1 positioned in the same odd number line 210-1 in a row, a second data hole line 261-2 for exposing the drain electrode 233-2 of the thin film transistor 230-2 positioned in the same even number line 210-2 in a row, and a second pin structure hole 262 for exposing the source electrode 234-2 of the thin film transistor 230-2 positioned in the same even number line 210-2 in a row.

More specifically, the first data hole line 261-1, first bias hole line 263-1, second data hole line 261-2, and second pin structure hole 262 may be created through an etching process after performing a process of exposing the first protective layer 250-1 to light.

Figure 2E:
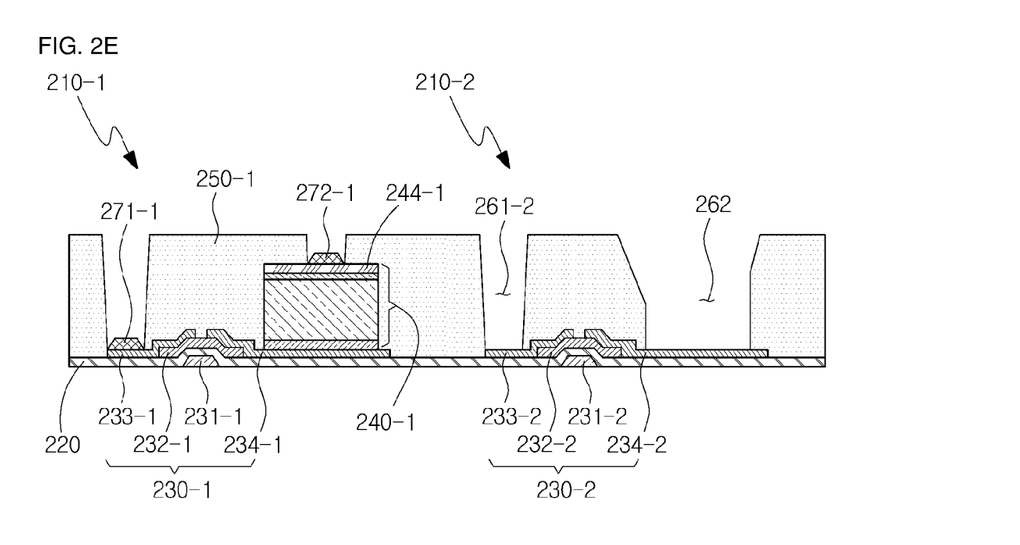

Thereafter, referring to FIG. 2E, there may be performed a step of forming a first data wire 271-1 in the first data hole line 261-1 and forming a first bias wire 272-1 in the first bias hole line 263-1.

More specifically, the first data wire 271-1 is electrically connected to the drain electrode 233-1 of the thin film transistor 230-1 positioned in the same odd number line 210-1, and the first bias wire 272-1 is electrically connected to the upper electrode 244-1 of the first pin structure 240-1 positioned in the same odd number line 210-1.

Figure 2F:
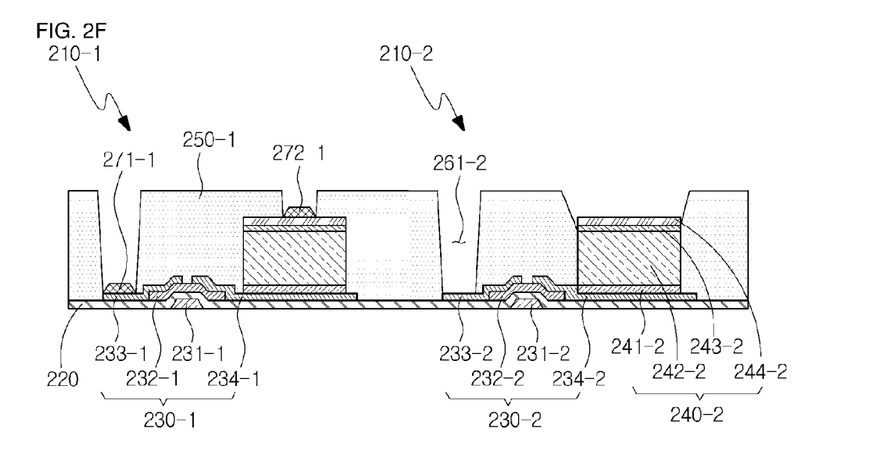

Thereafter, referring to FIG. 2F, it is possible to form the second pin structure 240-2 to be electrically connected to the source electrode 234-2 of each thin film transistor 230-2 exposed in the second pin structure hole 262.

More specifically, the second pin structure 240-2 includes a second N type semiconductor pattern 241-2 formed on a portion of the second source electrode 234-2 used as a lower electrode, a second intrinsic semiconductor pattern 242-2 formed on the second N type semiconductor pattern 241-2, a second P type semiconductor pattern 243-2 formed on the second intrinsic semiconductor pattern 242-2, and a second upper electrode 244-2 formed on the second P type semiconductor pattern 243-2. Herein, the second N type semiconductor pattern 241-2 may be made of N+ a-Si, the second intrinsic semiconductor pattern 242-2 may be made of a-Si, and the second P type semiconductor pattern 243-2 may be made of P+a-Si. Furthermore, the second upper electrode 244-2 may be made of a transparent electrode material.

Figure 2G:
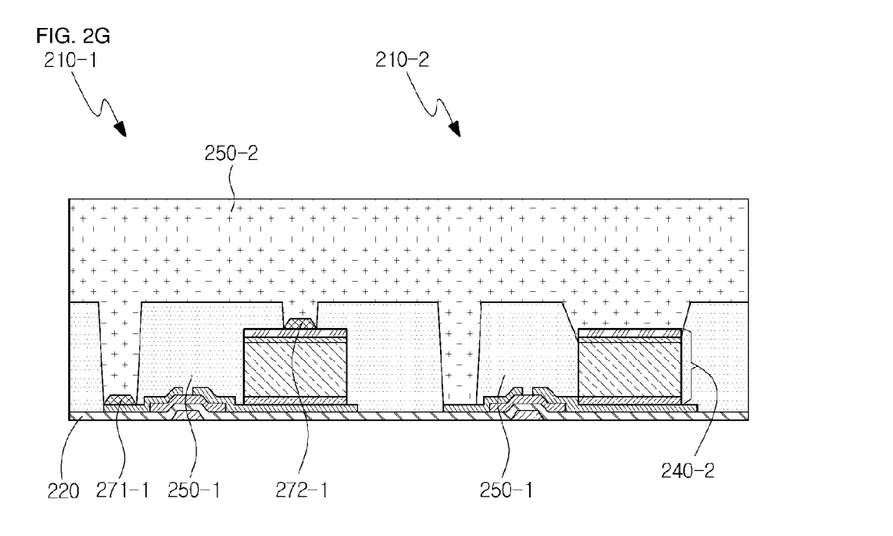

Thereafter, referring to FIG. 2G, there may be performed a step of forming a second protective layer 250-2 that covers an upper portion of the substrate 220 where the first data wire 271-1, first bias wire 272-1 and second pin structure 240-2 are formed.

Figure 2H:
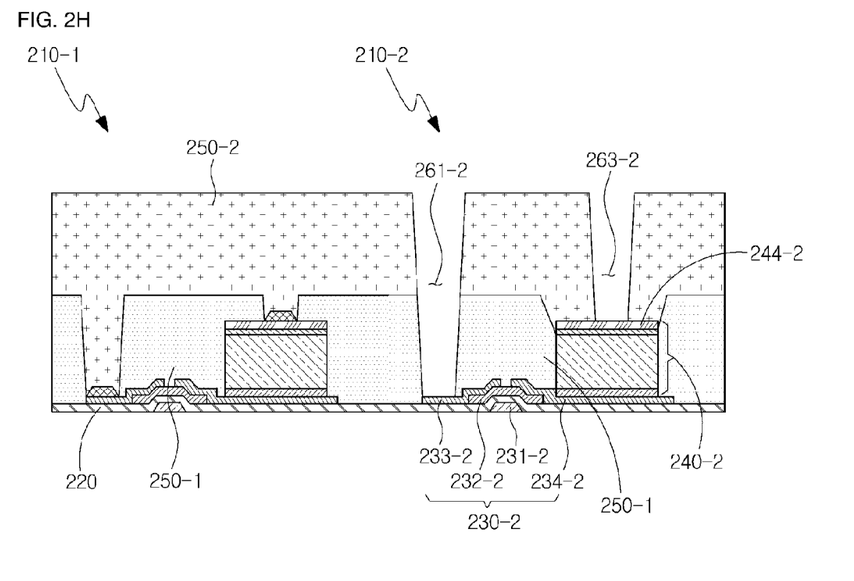

Thereafter, referring to FIG. 2H, there may be performed a step of forming, on the second protective layer 250-2, a second data hole line 261-2 for exposing the drain electrode 233-2 of the thin film transistor positioned in the same even number line 210-2 in a row, and a second bias hole line 263-2 for exposing the upper electrode 244-2 of the second pin structure 240-2 positioned in the same even number line 210-2 in a row.

More specifically, the second data hole line 261-2 and second bias hole line 263-2 may be formed through an etching process after performing a process of exposing the second protective layer 250-2 to light.

Figure 2I:
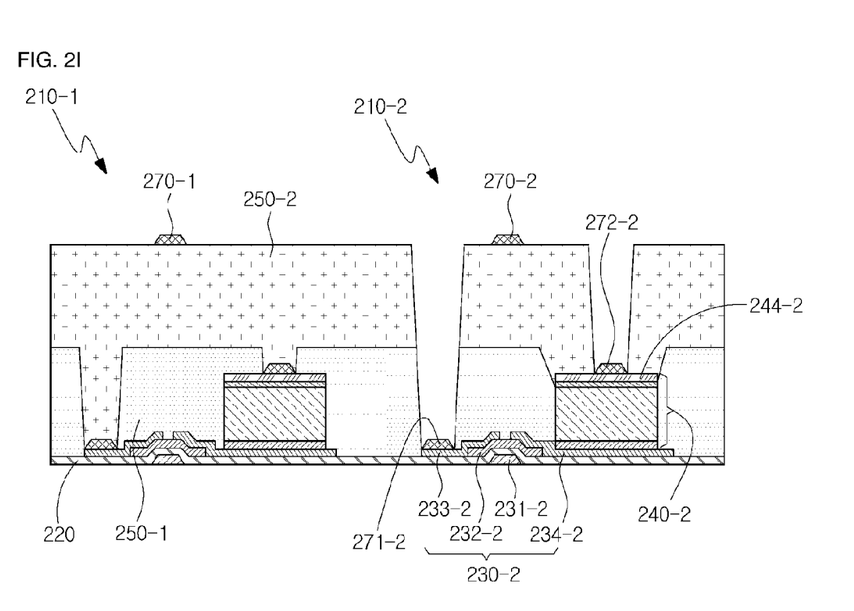

Thereafter, referring to FIG. 2I, there may be performed a step of forming a second data wire 271-2 on the second data hole line 261-2 and forming a second bias wire 272-2 on the second bias hole line 263-2.

More specifically, the second data wire 271-2 is electrically connected to the drain electrode 233-2 of the thin film transistor 230-2 positioned in the same even number line 210-2, and the second bias wire 272-2 is electrically connected to the upper electrode 244-2 of the second pin structure 240-2 positioned in the same even number line 210-2.

Furthermore, referring to FIG. 2I, there may be further performed a step of forming, on an upper portion of the second protective layer 250-2, a first and second light shield film 270-1, 270-2 for shielding upper portions 232-1, 232-2 of the active layers of the thin film transistors 230-1, 230-2.

Figure 2J:
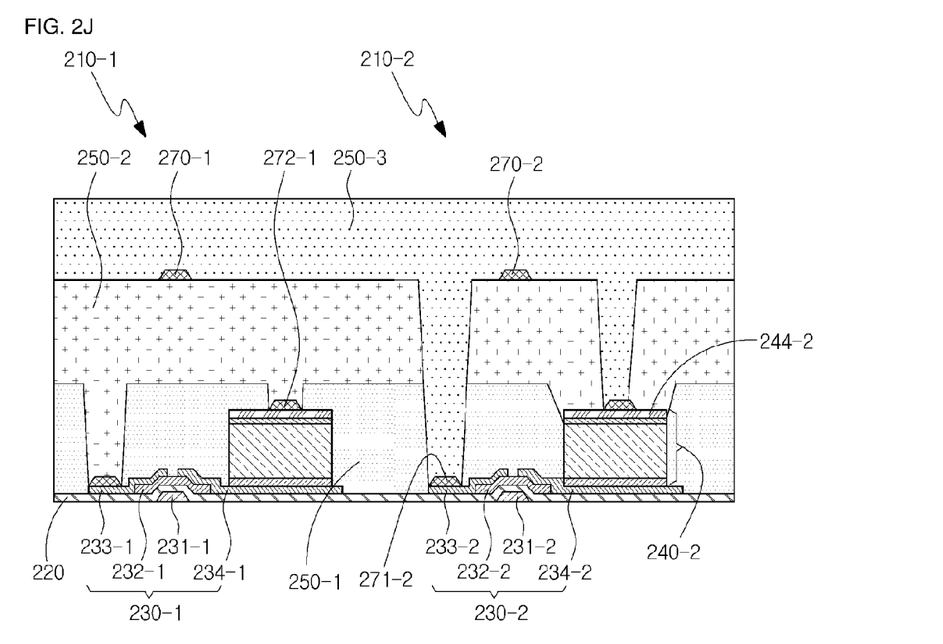

Furthermore, referring to FIG. 2J, there may be performed a step of forming a third protective layer 250-3 that covers an upper portion of the substrate where the second data wire 271-2 and second bias wire 272-2 are formed.

Hereinafter, a digital x-ray detector according to an embodiment of the present disclosure will be explained in detail with reference to FIG. 3.

Figure 3:
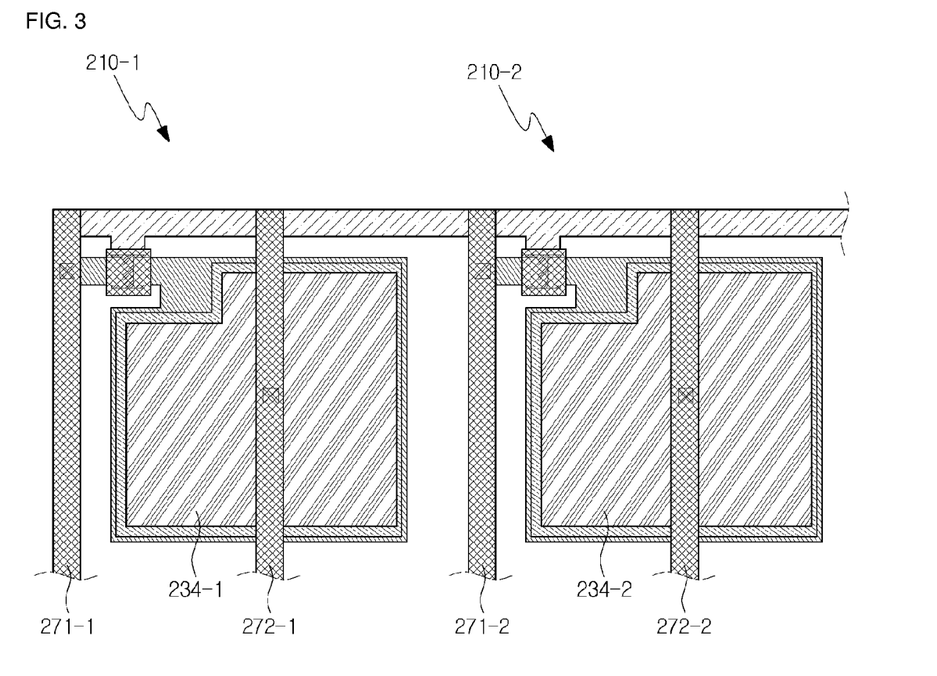
FIG. 3 is an exemplary plan view of a digital x-ray detector according to an embodiment of the present disclosure.

FIG. 3 is an exemplary plan view of a digital x-ray detector according to an embodiment of the present disclosure. Referring to FIG. 3, even if a particle (not illustrated) exists between an odd number line and even number line after the first upper electrode 234-1 is formed on the substrate of the odd number line, a conduction does not occur between the first upper electrode 234-1 and second upper electrode 234-2 by the particle (not illustrated).

Meanwhile, as explained in detail with reference to FIGS. 2 to 3, in the digital x-ray detector according to an embodiment of the present disclosure, even if there exists a particle (not illustrated) between an odd number line and even number line in a manufacturing process, by at least one of the first protective layer 250-1 to the third protective layer 250-3, the first upper electrode 234-1 of the first pin structure 240-1 formed in the same odd number line 210-1 and the second upper electrode 234-2 of the second pin structure 240-2 formed in the same even number line 210-2 are not electrically connected to each other through the particle (not illustrated).

Only certain characteristics of the present disclosure are illustrated and explained in the present specification, and various modifications and changes can be made by one skilled in the art. Therefore, it will be understood that the claims are intended to include changes and modifications within the spirit and scope of the present disclosure.

What is claimed is:

1. A method for manufacturing a digital x-ray detector wherein a plurality of sensing pixels are formed in a matrix structure, the method comprising:
  forming a thin film transistor on every sensing pixel area on an upper portion of a substrate;
  forming a first pin structure on each source electrode of the thin film transistor positioned in an odd number line;
  forming a first protective layer that covers an upper portion of the substrate where the first pin structures are formed;
  forming, on the first protective layer, a first data hole line that exposes a drain electrode of the thin film transistor positioned in the same odd number line in a row, a first bias hole line that exposes an upper electrode of the first pin structure positioned in the same odd number line in a row, a second data hole line that exposes a drain electrode of another thin film transistor positioned in the same even number line in a row, and a second pin structure hole that exposes a source electrode the another thin film transistor positioned in an even number line;

forming a first data wire inside the first data hole line, and forming a first bias wire inside the first bias hole line;

forming a second pin structure to be electrically connected to the source electrode of each of the another thin film transistor exposed inside the second pin structure hole;

forming a second protective layer that covers the upper portion of the substrate where the first data wire, first bias wire and second pin structure are formed;

forming, on the second protective layer, the second data hole line that exposes the drain electrode the another thin film transistor positioned in the same even number line in a row and a second bias hole line that exposes an upper electrode of the second pin structure positioned in the same line in a row; and forming a second data wire inside the second data hole line and forming a second bias wire inside the second bias hole line.

2. The method of claim 1, further comprising forming a light shield film that shields an upper portion of an active layer of the thin film transistor on an upper portion of the second protective layer, after the forming of the second protective layer.

3. The method of claim 2, wherein the light shield film is formed in a shape of a plurality of lines that shield the upper portion of the active layer of each thin film transistor positioned in the same odd number line and same even number line in a row.

4. The method of claim 3, wherein the light shield film is formed at the same step with the second data and second bias wire.

5. The method of claim 4, further comprising forming a third protective layer that covers the upper portion of the substrate where the second data wire and first bias wire are formed.

6. The method of claim 3, further comprising forming a third protective layer that covers the upper portion of the substrate where the second data wire and first bias wire are formed.

7. The method of claim 2, wherein the light shield film is formed at the same step with the second data wire and second bias wire.

8. The method of claim 7, further comprising forming a third protective layer that covers the upper portion of the substrate where the second data wire and first bias wire are formed.

9. The method of claim 2, further comprising forming a third protective layer that covers the upper portion of the substrate where the second data wire and first bias wire are formed.

10. The method of claim 1, further comprising forming a third protective layer that covers the upper portion of the substrate where the second data wire and first bias wire are formed.

11. A digital x-ray detector where a plurality of units of sensing pixels are formed in a matrix structure, the detector comprising:
a thin film transistor formed on every sensing pixel area on an upper portion of a substrate;
a first pin structure formed on each source electrode of the thin film transistor positioned in an odd number line;
a second pin structure formed on each source electrode of the another thin film transistor positioned in an even number line;
a first data wire that connects a drain electrode of the thin film transistor positioned in the same odd number line in a row;
a second data wire that connects a drain electrode the another thin film transistor positioned in the same even number line in a row;
a first bias wire that connects an upper electrode of the first pin structure positioned in the same odd number line in a row;
a second bias wire that connects an upper electrode of the second pin structure positioned in the same even number line in a row; and
a first protective layer that covers the upper portion of the substrate where the thin film transistor and the first pin structure are formed,
wherein the second pin structure is formed inside a hole formed in the first protective layer.

12. The digital x-ray detector of claim 11, wherein the first data wire and the first bias wire are formed inside a hole line formed in the first protective layer.

13. The digital x-ray detector of claim 11, further comprising a second protective layer formed on an upper portion of the first protective layer,
wherein the second data wire is formed inside a hole line formed to penetrate the first protective layer and the second protective layer, and
the second bias wire is formed inside the hole line formed in the second protective layer.

14. The digital x-ray detector of claim 13, wherein a light shield film that shields an upper portion of an active layer of the thin film transistor is further formed on an upper portion of the second protective layer.

15. The digital x-ray detector of claim 14, wherein the light shield film is formed in a shape of a plurality of lines that shield the upper portion of the active layer of the thin film transistor positioned in the same odd number line and the same even number line in a row.

16. The digital x-ray detector of claim 15, further comprising a third protective layer formed on the upper portion of the second protective layer.

17. The digital x-ray detector of claim 14, further comprising a third protective layer formed on the upper portion of the second protective layer.

18. The digital x-ray detector of claim 13, further comprising a third protective layer formed on an upper portion of the second protective layer.

* * * * *